US006955649B2

(12) United States Patent
Narimatsu

(10) Patent No.: US 6,955,649 B2
(45) Date of Patent: Oct. 18, 2005

(54) ARTERIOSCLEROSIS EVALUATING APPARATUS

(75) Inventor: Kiyoyuki Narimatsu, Komaki (JP)

(73) Assignee: Colin Medical Technology Corporation, Komaki (JP)

( * ) Notice: Subject to any disclaimer, the term of this patent is extended or adjusted under 35 U.S.C. 154(b) by 644 days.

(21) Appl. No.: 10/194,007

(22) Filed: Jul. 15, 2002

(65) Prior Publication Data

US 2003/0130578 A1 Jul. 10, 2003

(30) Foreign Application Priority Data

Jan. 9, 2002 (JP) .............................. 2002-001931

(51) Int. Cl.[7] .............................................. A61B 05/02
(52) U.S. Cl. ...................... 600/483; 600/485; 600/500; 600/481
(58) Field of Search ............................... 600/481, 483, 600/485, 490, 492–496, 500–503

(56) References Cited

U.S. PATENT DOCUMENTS

| 5,261,414 | A | 11/1993 | Aung et al. | |
|---|---|---|---|---|
| 5,309,916 | A | 5/1994 | Hatschek | |
| 6,355,000 | B1 | 3/2002 | Ogura | |
| 6,612,993 | B2 * | 9/2003 | Narimatsu | 600/500 |
| 6,659,958 | B2 * | 12/2003 | Narimatsu et al. | 600/485 |
| 6,719,704 | B2 * | 4/2004 | Narimatsu et al. | 600/500 |
| 6,786,872 | B2 * | 9/2004 | Narimatsu et al. | 600/490 |
| 6,793,628 | B2 * | 9/2004 | Ogura et al. | 600/490 |
| 6,827,687 | B2 * | 12/2004 | Narimatsu et al. | 600/485 |

FOREIGN PATENT DOCUMENTS

| JP | A 08-187227 | 7/1996 |
|---|---|---|
| JP | A 2002-316821 | 10/2002 |
| WO | WO 01/70106 A1 | 9/2001 |

* cited by examiner

Primary Examiner—Robert L. Nasser
Assistant Examiner—Navin Natnithithadha
(74) Attorney, Agent, or Firm—Oliff & Berridge, PLC

(57) ABSTRACT

An apparatus for evaluating arteriosclerosis of a living subject, including a blood-pressure measuring device which measures at least one blood-pressure value of the subject, a pulse-wave detecting device which detects a pulse wave from a portion of the subject, a relationship determining device for determining a relationship between pulse-wave magnitude and blood pressure, based on at least one magnitude of the pulse wave detected by the pulse-wave detecting device and said at least one blood-pressure value measured by the blood-pressure measuring device, an incident-wave-peak determining device for determining a magnitude of a peak point of an incident-wave component which is contained in the pulse wave detected by the pulse-wave detecting device, a reflected-wave-occurrence-time determining device for determining a time of occurrence of a peak point of a reflected-wave component which is contained in the pulse wave, a pressure-difference determining device for determining, according to the relationship between pulse-wave magnitude and blood pressure, a pressure difference corresponding to a magnitude difference between a magnitude of the pulse wave at the time of occurrence of the peak point of the reflected-wave component, and the magnitude of the peak point of the incident-wave component, and a display device which displays the pressure difference determined by the pressure-difference determining device.

9 Claims, 9 Drawing Sheets

ARTERIOSCLEROSIS EVALUATING APPARATUS

BACKGROUND OF THE INVENTION

1. Field of the Invention

The present invention relates to an arteriosclerosis evaluating apparatus which evaluates arteriosclerosis of a living subject based on afterload acting on the subject's heart.

2. Related Art Statement

Pulse-wave propagation velocity or pulse-wave augmentation index is known as an index used to evaluate arteriosclerosis of a living person. Pulse-wave propagation velocity is a velocity at which a pulse wave propagates between two portions of a person, and it increases as the person's arteriosclerosis advances. Pulse-wave augmentation index, known as AI, is generally determined as a percentage of a value obtained by dividing a magnitude difference between a magnitude of a pulse wave at the time of occurrence of a reflected-wave component of the pulse wave and a magnitude of a peak point of an incident-wave component of the pulse wave, by a pulse pressure of the pulse wave, and there is a tendency that this index increases as arteriosclerosis advances.

In addition, cardiac afterload, i.e., afterload acting on person's heart changes in relation with arteriosclerosis. The cardiac afterload is known as a load that is exerted to the heart by the resistance of peripheral blood vessels, such as aorta and arterioles. The reason why cardiac afterload relates to arteriosclerosis is that the harder the arteries are, the greater the resistance of the blood vessels is and accordingly the harder the arteries are, the greater the load acting on the heart at the time of ejecting blood is.

Cardiac afterload provides different information about evaluation of arteriosclerosis, than the information provided by the conventional arteriosclerosis-evaluation indexes such as pulse-wave propagation velocity or pulse-wave augmentation index. Thus, it is expected that if cardiac afterload is used either solely or in combination with one or more conventional arteriosclerosis-evaluation indexes such as pulse-wave propagation velocity or pulse-wave augmentation index, arteriosclerosis can be evaluated with higher accuracy.

However, as described above, cardiac afterload is a load exerted to person's heart by resistance of peripheral blood vessels, and accordingly it is difficult to directly measure it. Thus, there has not been practiced to measure cardiac afterload and evaluate arteriosclerosis based on the measured afterload.

SUMMARY OF THE INVENTION

It is therefore an object of the present invention to provide an arteriosclerosis evaluating apparatus which can evaluate arteriosclerosis of a living subject based on afterload acting on the subject's heart.

The Inventor has carried out extensive studies to achieve the above object, and has obtained the following knowledge:

Pulse-wave augmentation index is a parameter representing a proportion of a reflected wave of a pulse wave to an incident wave thereof, and is generally calculated as a percentage of a value obtained by dividing a magnitude difference between a magnitude of the pulse wave at the time of occurrence of the reflected wave and a magnitude of a peak point of the incident wave, by a pulse pressure of the pulse wave, as described above. That is, the magnitude difference is used as a magnitude of the reflected wave. Since the magnitude of the reflected wave corresponds to a pressure returning to the heart, the magnitude of the reflected wave represents an afterload acting on the heart. Therefore, the magnitude difference changes in relation with the cardiac afterload. On the other hand, the magnitude of the pulse wave changes in relation with the blood pressure, but it cannot be directly converted into a blood-pressure value. Thus, the magnitude difference cannot be directly converted into the pressure corresponding to the magnitude of the reflected wave.

Here, if a blood-pressure value of the person is measured and, based on the measured blood-pressure value, a magnitude of a pulse wave can be converted into a corresponding blood-pressure value, the above-indicated magnitude difference can also be converted into a corresponding pressure and accordingly a cardiac afterload corresponding to the pressure can be determined. The present invention has been developed based on this knowledge.

The above object has been achieved by the present invention. According to the present invention, there is provided an apparatus for evaluating arteriosclerosis of a living subject, comprising a blood-pressure measuring device which measures at least one blood-pressure value of the subject; a pulse-wave detecting device which detects a pulse wave from a portion of the subject; a relationship determining means for determining a relationship between pulse-wave magnitude and blood pressure, based on at least one magnitude of the pulse wave detected by the pulse-wave detecting device and the at least one blood-pressure value measured by the blood-pressure measuring device; an incident-wave-peak determining means for determining a magnitude of a peak point of an incident-wave component which is contained in the pulse wave detected by the pulse-wave detecting device; a reflected-wave-occurrence-time determining means for determining a time of occurrence of a peak point of a reflected-wave component which is contained in the pulse wave detected by the pulse-wave detecting device; a pressure-difference determining means for determining, according to the relationship between pulse-wave magnitude and blood pressure, determined by the relationship determining means, a pressure difference corresponding to a magnitude difference between a magnitude of the pulse wave at the time of occurrence of the peak point of the reflected-wave component, determined by the reflected-wave-occurrence-time determining means, and the magnitude of the peak point of the incident-wave component, determined by the incident-wave-peak determining means; and a display device which displays the pressure difference determined by the pressure-difference determining means.

According to this invention, the pressure-difference determining means determines the pressure difference corresponding to the magnitude difference between the magnitude of the pulse wave at the time of occurrence of the peak point of the reflected-wave component, determined by the reflected-wave-occurrence-time determining means, and the magnitude of the peak point of the incident-wave component of the pulse wave. This pressure difference can be used as the pressure corresponding to the reflected-wave component. Therefore, based on the pressure difference displayed on the display device, a person such as a doctor can evaluate afterload acting on the subject's heart. In addition, since increased cardiac afterload indicates advanced arteriosclerosis, the person can also evaluate arteriosclerosis of the subject based on the pressure difference.

According to a preferred feature of the present invention, the arteriosclerosis evaluating apparatus further comprises a blood-pressure-related-information obtaining device which obtains blood-pressure-related information which changes in relation with blood pressure of the subject; a memory device which stores a plurality of sets of display information each of which includes a pressure difference determined by the pressure-difference determining means and a piece of blood-pressure-related information obtained by the blood-pressure-related-information obtaining device; and a graph displaying means for operating the display device to display a two-dimensional graph defined by a first axis indicative of pressure difference and a second axis indicative of blood-pressure-related information, and additionally display a plurality of symbols at a plurality of positions, respectively, which correspond to said plurality of sets of display information, respectively, that are stored by the memory device.

According to this feature, the memory device stores the plurality of sets of display information each of which includes a pressure difference determined by the pressure-difference determining means and, e.g., a blood-pressure value measured by the blood-pressure measuring device, and the graph displaying means operates the display device to display, in a two-dimensional graph, a plurality of symbols at a plurality of positions corresponding to the plurality of sets of display information stored by the memory device. Thus, based on what is displayed by the display device, a person such as a doctor can easily observe, in the second or subsequent measuring operations, a time-wise change of the pressure difference with respect to a time-wise change of the blood pressure and accordingly can easily recognize the virtue of treatment against the subject's arteriosclerosis.

BRIEF DESCRIPTION OF THE DRAWINGS

The above and optional objects, features, and advantages of the present invention will be better understood by reading the following detailed description of the preferred embodiments of the invention when considered in conjunction with the accompanying drawings, in which.

DETAILED DESCRIPTION OF PREFERRED EMBODIMENTS

Figure 1:
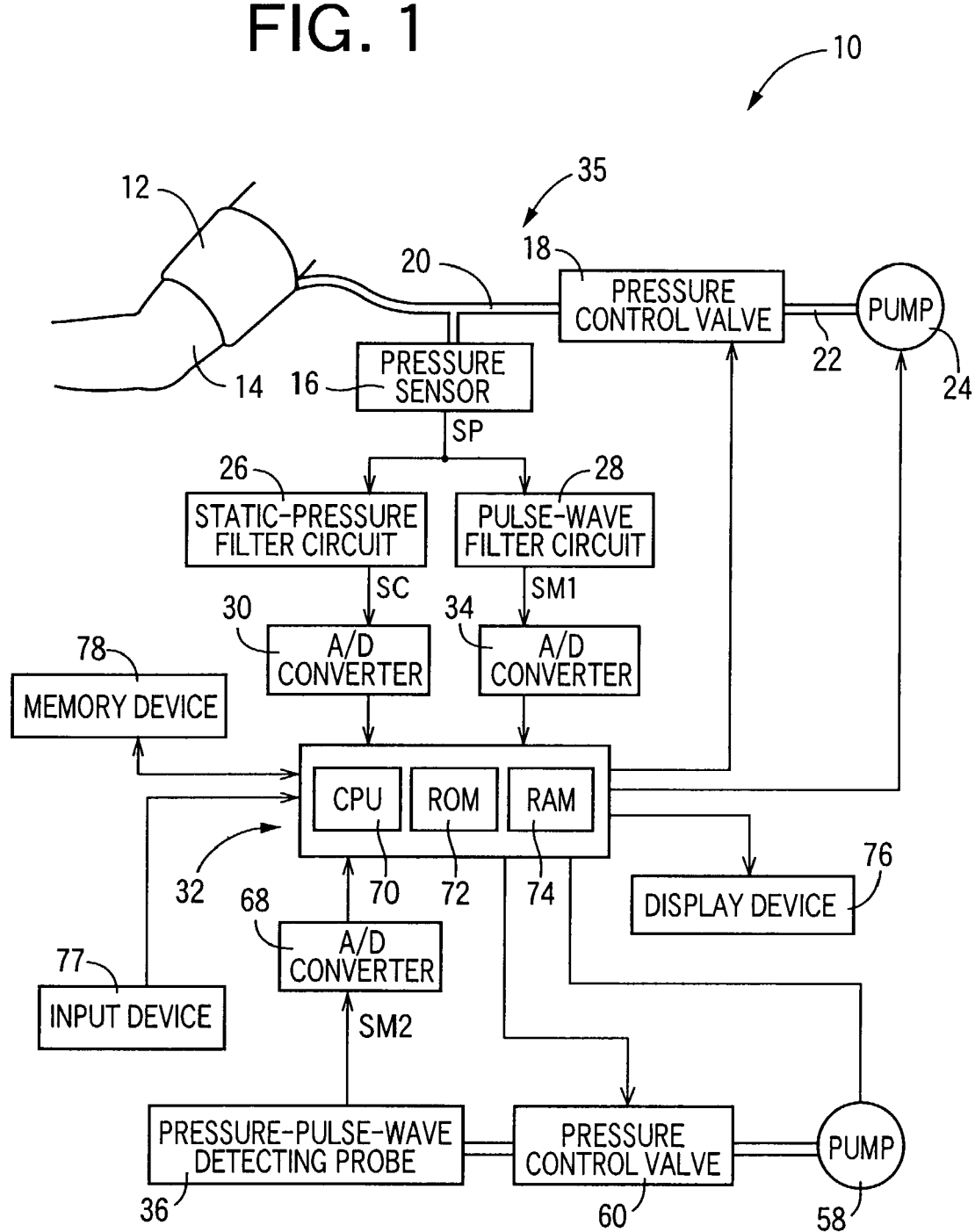
FIG. 1 is a diagrammatic view showing a circuitry of an arteriosclerosis evaluating apparatus to which the present invention is applied.

Hereinafter, there will be described an embodiment of the present invention in detail by reference to the drawings. FIG. 1 is a diagrammatic view showing a circuitry of an arteriosclerosis evaluating apparatus 10 to which the present invention is applied.

In FIG. 1, reference numeral 12 designates an inflatable cuff which includes a belt-like cloth bag and a rubber bag accommodated in the cloth bag and which is adapted to be wound around an upper portion 14 of, e.g., a right arm of a patient as a living subject. The cuff 12 is connected via a piping 20 to a pressure sensor 16 and a pressure control valve 18. The pressure control valve 18 is connected via a piping 22 to an air pump 24. The pressure control valve 18 adjusts a pressure of a pressurized air supplied from the air pump 24, and supplies the pressure-adjusted air to the cuff 12, or discharges the pressurized air from the cuff 12, so as to control an air pressure in the cuff 12.

The pressure sensor 16 detects the air pressure in the cuff 12, and supplies a pressure signal, SP, representing the detected air pressure, to a static-pressure filter circuit 26 and a pulse-wave filter circuit 28. The static-pressure filter circuit 26 includes a low-pass filter which extracts, from the pressure signal SP, a cuff-pressure signal, SC, representing a static component of the detected air pressure, i.e., a pressing pressure of the cuff 12 (hereinafter, referred to as the cuff pressure, PC). The filter circuit 26 supplies the cuff-pressure signal SC to an electronic control device 32 via an A/D (analog-to-digital) converter 30. The pulse-wave filter circuit 28 includes a band-pass filter which extracts, from the pressure signal SP, a cuff-pulse-wave signal, SM1, representing a cuff pulse wave as an oscillatory component of the detected air pressure that has prescribed frequencies. The filter circuit 28 supplies the cuff-pulse-wave signal SM1 to the control device 32 via an A/D converter 34. The control device 32 determines blood-pressure values BP of the patient, based on the cuff-pressure signal SC and the cuff-pulse-wave signal SM1, as described later. Thus, the control device 32 cooperates with the cuff 12, the pressure sensor 16, the static-pressure filter circuit 26, the pulse-wave filter circuit 28, the pressure control valve 18, the air pump 24, etc. to provide a blood-pressure measuring device 35.

Figure 2:
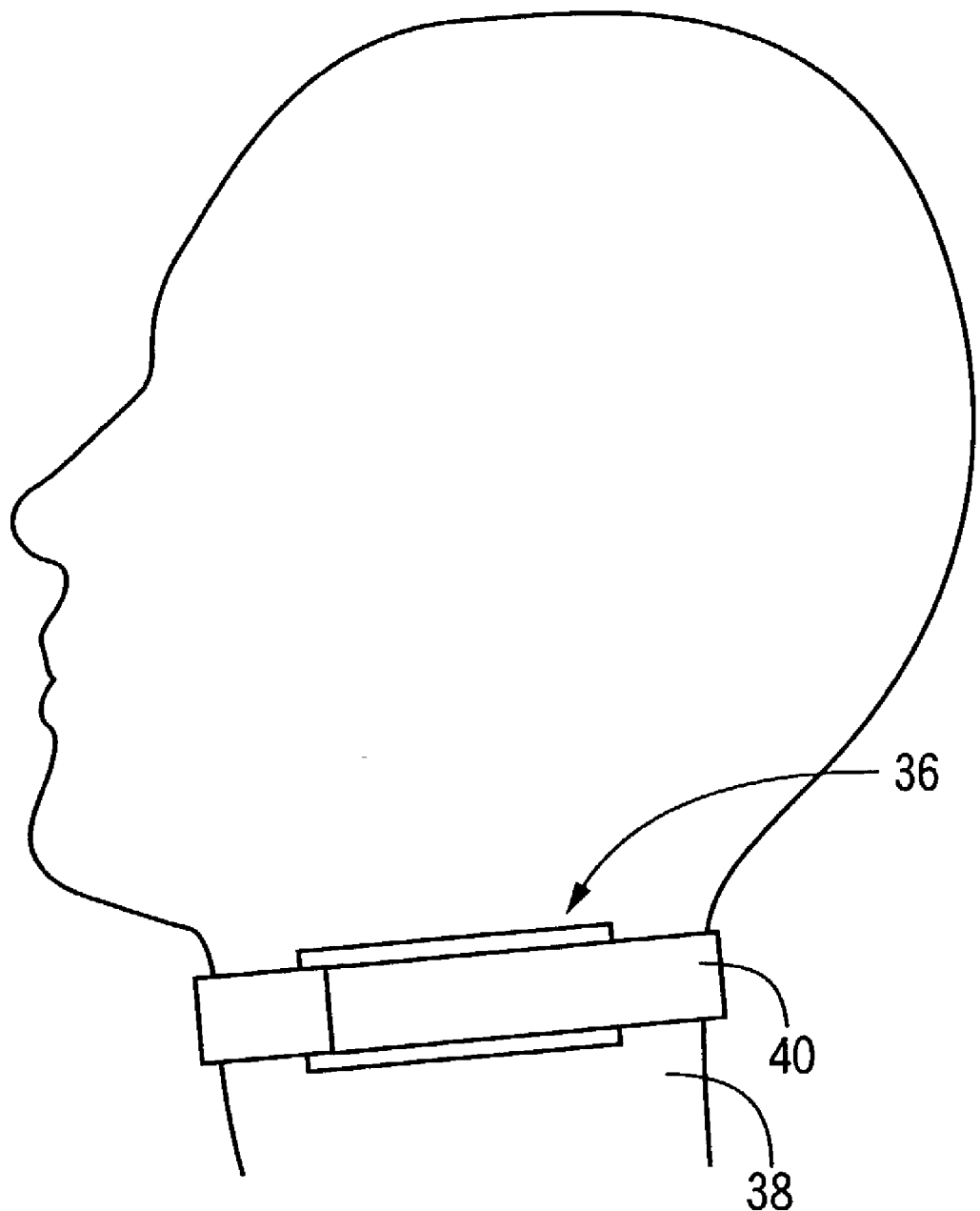
FIG. 2 is an illustrative view showing a state in which a pressure-pulse-wave detecting probe of the apparatus of FIG. 1 is worn on a neck portion of a living subject.
Figure 3:
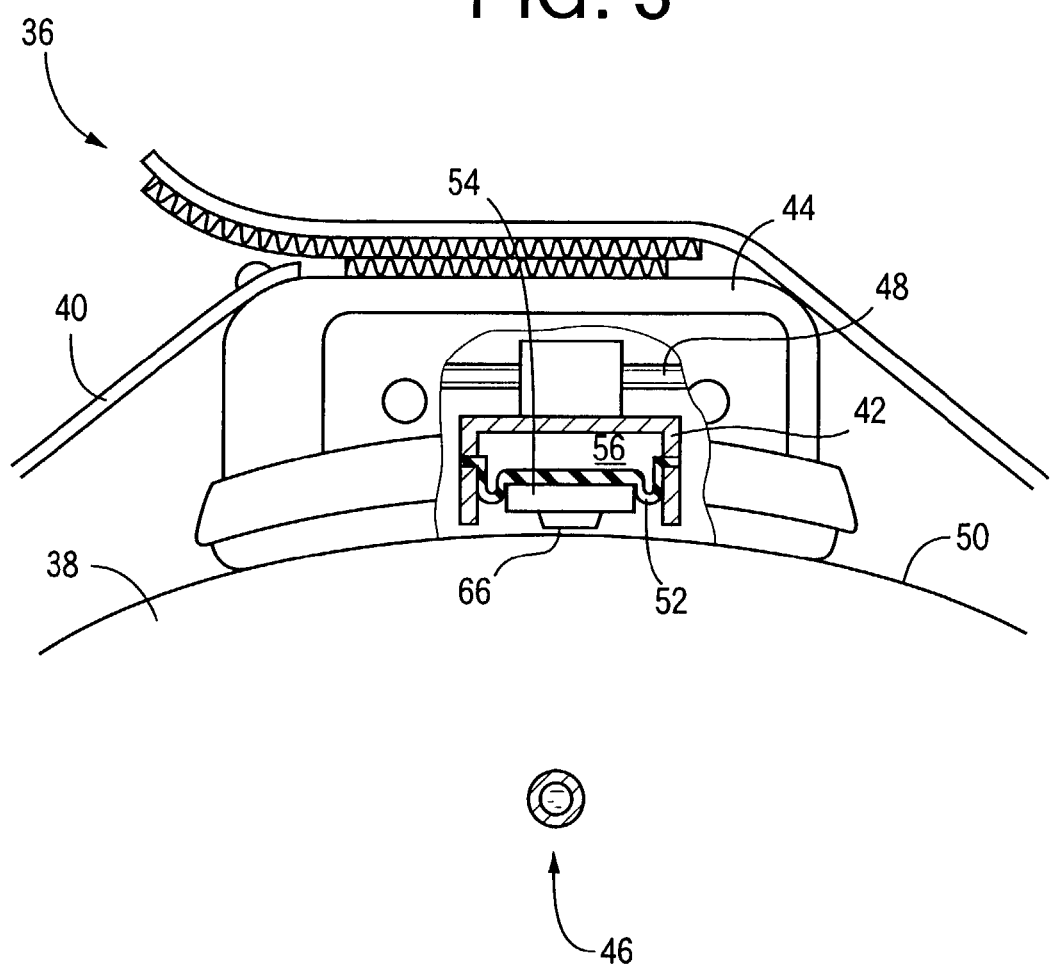
FIG. 3 is an enlarged view of the pressure-pulse-wave detecting probe of FIG. 2, a portion of the probe being cut away.

The present arteriosclerosis evaluating apparatus 10 includes a pressure-pulse-wave detecting probe 36, shown in FIG. 2, that functions as a pulse-wave detecting device. The pressure-pulse-wave detecting probe 36 is worn on a neck portion 38 of the subject, as illustrated in FIG. 2, with the help of a band 40. As shown in detail in FIG. 3, the pressure-pulse-wave detecting probe 36 includes a container-like sensor housing 42; a case 44 which accommodates the sensor housing 42; and a feed screw 48 which is threadedly engaged with the sensor housing 42 and is rotated by an electric motor, not shown, provided in the case 44 so as to move the sensor housing 42 in a widthwise direction of a carotid artery 46. With the help of the band 40, the pressure-pulse-wave detecting probe 36 is detachably attached to the neck portion 38, such that an open end of the sensor housing 42 is opposed to a body surface 50 of the neck portion 38.

In addition, the pressure-pulse-wave detecting probe 36 includes a pressure-pulse-wave sensor 54 which is secured via a diaphragm 52 to an inner wall of the sensor housing 42, such that the sensor 54 is movable relative to the housing 42 and is advanceable out of the open end of the same 42. The sensor housing 42, the diaphragm 52, etc. cooperate with one another to define a pressure chamber 56, which is supplied with a pressurized air from an air pump 58 via a pressure-control valve 60, as shown in FIG. 1, so that the pressure-pulse-wave sensor 54 is pressed against the body surface 50 with a pressing force corresponding to the air pressure in the pressure chamber 56.

The sensor housing 42 and the diaphragm 52 cooperate with each other to provide a pressing device 62 which presses the pressure-pulse-wave sensor 54 against the carotid artery 46, and the feed screw 48 and the not-shown motor cooperate with each other to provide a widthwise-direction moving device 64 which moves the pressure-pulse-wave sensor 54 in the widthwise direction of the carotid artery 46 and thereby changes a pressing position where the sensor 54 is pressed on the body surface 50.

Figure 4:
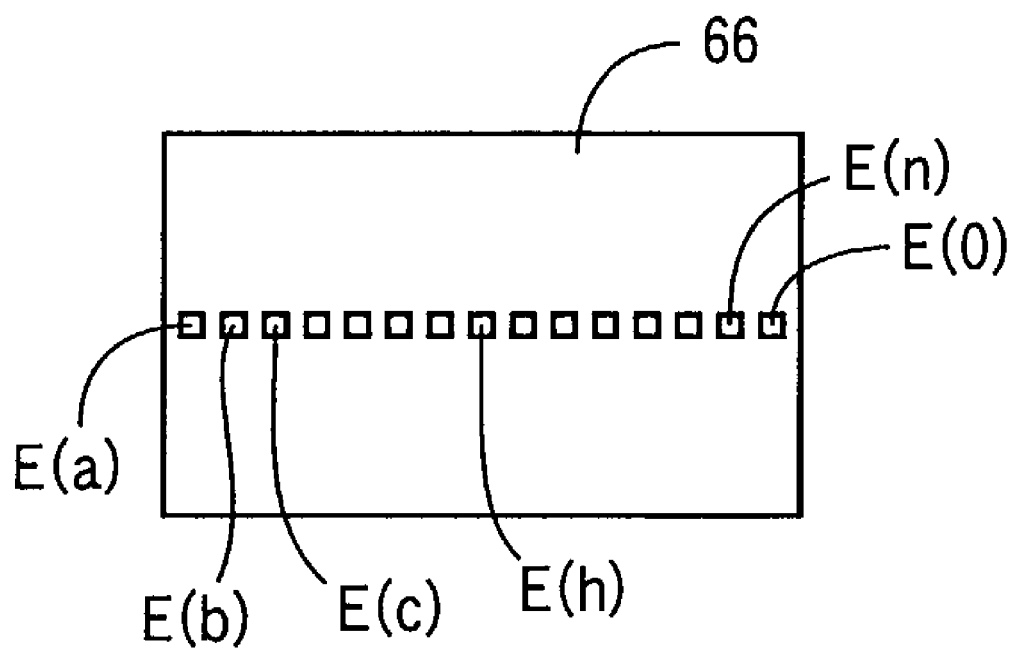
FIG. 4 is a view for explaining a state in which an array of pressure-sensing elements is provided in a press surface of a pressure-pulse-wave sensor shown in FIG. 1.

The pressure-pulse-wave sensor 54 has a pressing surface 66, and a number of semiconductor pressure-sensing elements (hereinafter, referred to as the "pressure-sensing elements") E which are arranged in the pressing surface 66 at a regular interval in the widthwise direction of the carotid artery 46, i.e., in the direction of movement of the sensor 54 parallel to the feed screw 48, over a length greater than the diameter of the carotid artery 46. For example, as shown in FIG. 4, fifteen pressure-sensing elements E(a), E(b), . . . , E(o) are arranged at a regular interval of; e.g., 0.6 mm.

The pressure-pulse-wave detecting probe 36, constructed as described above, is pressed against the body surface 50 of the neck portion 38 right above the carotid artery 46, so that the pressure-pulse-wave sensor 54 detects a pressure pulse wave (i.e., a carotid pulse wave, wc) which is produced from the carotid artery 46 and is propagated to the body surface 50, and supplies a pressure-pulse-wave signal SM2 representing the detected carotid pulse wave wc, to the control device 32 via an A/D converter 68. An example of the carotid pulse wave wc represented by the pressure-pulse-wave signal SM2 continuously supplied from the pressure-pulse-wave sensor 30 is indicated at solid line in FIG. 5.

The control device 32 is provided by a so-called microcomputer including a CPU (central processing unit) 70, a ROM (read only memory) 72, a RAM (random access memory) 74, and an I/O (input-and-output) port, not shown. The CPU 70 processes signals according to the control programs pre-stored in the ROM 72 by utilizing the temporary-storage function of the RAM 74, and supplies drive signals via the I/O port to the air pumps 24, 58 and the pressure control valves 18, 60 so as to control the cuff pressure PC and the pressure in the pressure chamber 56. Moreover, the CPU 48 determines a pressure difference, ΔP, as will be described below in connection with the control functions illustrated in detail in FIG. 6, and controls what is displayed by a display device 76.

An input device 77 includes a keyboard, not shown, through which an identification number for identifying each patient from other patients is inputted by a medical person or the patient. The input device 77 supplies a signal representing the identification number, to the control device 32. A memory device 78, which is provided by a well-known memory means such as a magnetic disk, a magnetic tape, a volatile semiconductor memory, or a non-volatile semiconductor memory, stores the blood-pressure values BP and the pressure difference ΔP determined by the control device 32 for each patient, such that the blood-pressure values BP and the pressure difference ΔP are associated with the identification number of the patient.

Figure 6:
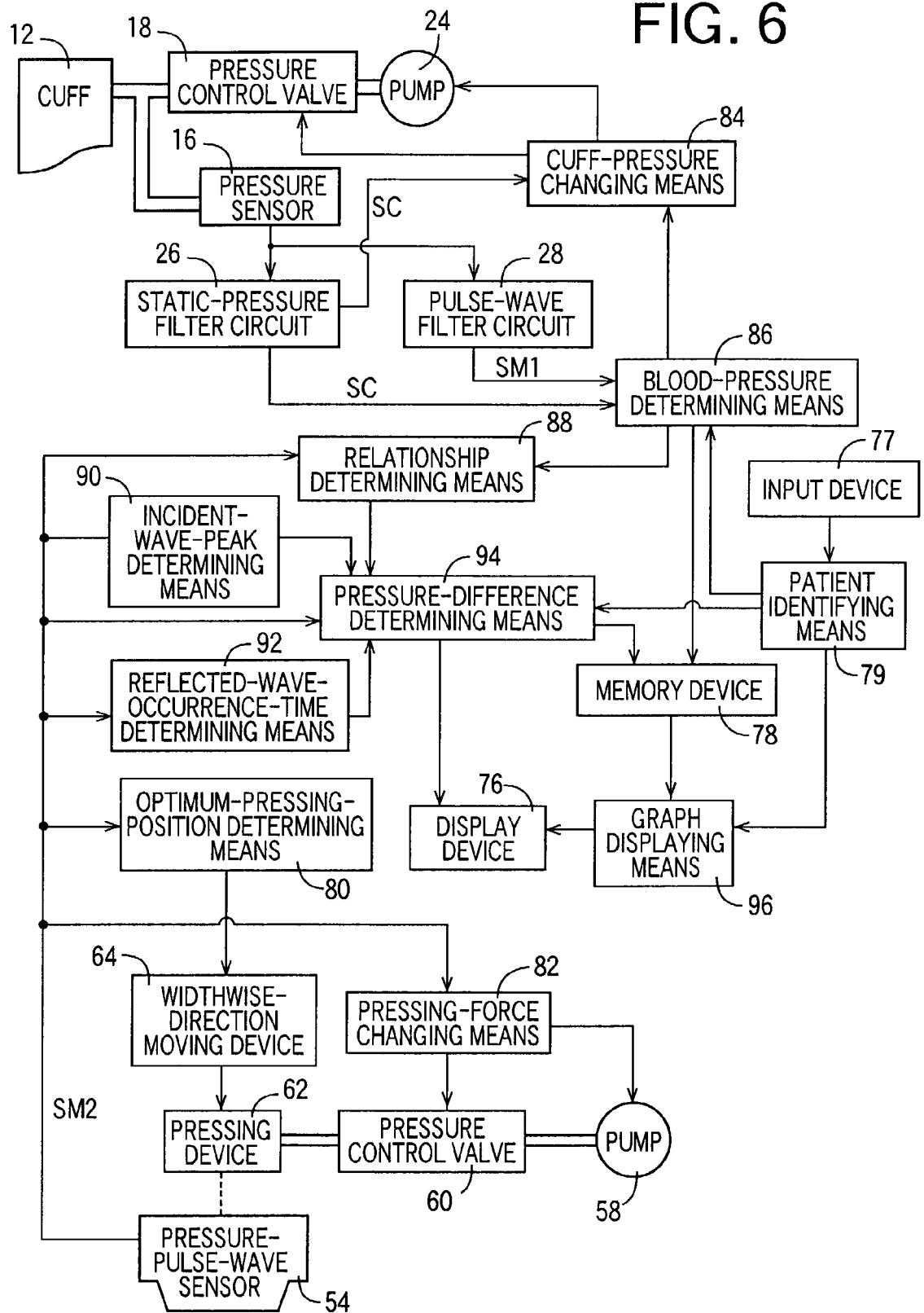
FIG. 6 is a block diagram for explaining essential control functions of an electronic control device of the apparatus of FIG. 1.

FIG. 6 is a block diagram for explaining the essential control functions of the control device 32 of the arteriosclerosis evaluating apparatus 10. A patient identifying means 79 identifies, based on the identification number represented by the signal supplied from the input device 77, the patient whose blood-pressure values BP and pressure difference ΔP are to be measured by the apparatus 10.

An optimum-pressing-position determining means 80 judges whether a prescribed pressing-position changing condition is satisfied, i.e., whether one (hereinafter, referred to as the "highest-pressure detecting element EM") of the pressure-sensing elements E of the pressure-pulse-wave sensor 54 that detects the highest pressure of the respective pressures detected by all the elements E is positioned in one of prescribed opposite end portions of the array of pressure-sensing elements E. Each of the prescribed opposite end portions of the array of elements E may be a range having a prescribed length including a corresponding one of the opposite ends of the array of elements E, or a range accommodating a prescribed number of elements E including a corresponding one of the respective elements E located at the opposite ends of the array. The highest-pressure detecting element EM is one of the elements E that is positioned right above the carotid artery 46. When this pressing-position changing condition is satisfied, the optimum-pressing-position determining means 80 carries out the following pressing-position changing operation: After the pressing device 62 once moves the pressure-pulse-wave sensor 54 away from the body surface 50, the widthwise-direction moving device 64 moves the pressing device 62 and the sensor 54 over a prescribed distance, and then the pressing device 62 again presses the sensor 54 with a prescribed, considerably low first pressing force HDP1. In this state, the determining means 80 judges again whether the prescribed pressing-position changing condition is satisfied. The determining means 80 repeats carrying out the above-described operation and judgment till the pressing-position changing condition is not satisfied any longer, preferably till the highest-pressure detecting element EM is positioned in a prescribed middle portion of the array of elements E. The length, or element number, employed for each of the opposite end portions of the array of elements E is prescribed based on the diameter of the artery (i.e., the carotid artery 46) to be pressed by the pressure-pulse-wave sensor 54, and may be one fourth of the diameter.

A pressing-force changing means 82 changes, after the optimum-pressing-position determining means 80 positions the pressure-pulse-wave sensor 54 at the optimum pressing position, a pressing force HDP (i.e., a hold-down pressure) applied by the pressing device 62 to the sensor 54, within a prescribed pressing-force range, either stepwise in response to each heartbeat of the subject or continuously at a prescribed, considerably low rate. Based on the carotid pulse wave wc obtained during the changing of the pressing force HDP, the changing means 82 determines an optimum pressing force HDPO and maintains the pressing force applied by the pressing device 62 to the sensor 54, at the thus determined optimum pressing force HDPO. Here, the optimum pressing force HDPO is so determined that a pulse pressure PPc of the carotid pulse wave wc detected by the highest-pressure detecting element EM pressed by the pressing force HDP (i.e., a difference obtained by subtracting a minimal magnitude, from a maximal magnitude, of one heartbeat-synchronous pulse of the carotid pulse wave wc) may not be smaller than a predetermined lower-limit pulse pressure $PPc_L$. The lower-limit pulse pressure $PPc_L$ is experimentally predetermined as a value which assures that a clear carotid pulse wave wc can be detected. If the pulse pressure PPc is too small, a clear carotid pulse wave wc cannot be obtained.

A cuff-pressure changing means 84 operates, based on the cuff-pressure signal SC supplied from the static-pressure filter circuit 26, the pressure control valve 18 and the air pump 24 so as to quickly increase the cuff pressure PC to a prescribed target pressure $PC_M$ (e.g., 180 mmHg) that would be higher than a systolic blood pressure $BP_{SYS}$ of the patient and, subsequently, slowly decrease the cuff pressure at a rate of, e.g., 2 or 3 mmHg/sec. After a blood-pressure determining means 86, described below, determines blood-pressure values BP of the patient, the changing means 84 releases the cuff pressure PC to an atmospheric pressure.

The blood-pressure determining means 86 determines, based on the cuff-pressure signal SC continuously supplied from the static-pressure filter circuit 26, and the cuff-pulse-wave signal SM1 continuously supplied from the pulse-wave filter circuit 28, each during the slow decreasing of the cuff pressure PC under the control of the cuff-pressure changing means 84, a systolic blood pressure $BP_{SYS}$, a mean blood pressure $BP_{MEAN}$, and a diastolic blood pressure $BP_{DIA}$ of the patient, according to well-known oscillometric method. In addition, the determining means 86 stores, in the memory device 78, the thus determined blood-pressure values BP as the blood-pressure values BP of the patient identified by the patient identifying means 79, together with data indicative of a date and a time when the blood-pressure values BP are measured. The blood-pressure values BP are a sort of blood-pressure-related information, and accordingly the blood-pressure determining means 86 functions as a blood-pressure-related-information obtaining means.

A relationship determining means 88 determines a relationship between magnitude of carotid pulse wave and blood pressure that is to be used to convert a magnitude of the carotid pulse wave wc detected by the pressure-pulse-wave sensor 54, into a blood-pressure value BP. More specifically described, the systolic blood pressure $BP_{SYS}$, the mean blood pressure $BP_{MEAN}$, and the diastolic blood pressure $BP_{DIA}$, determined by the blood-pressure determining means 86, correspond to a magnitude of a peak, b, of one heartbeat-synchronous pulse of the carotid pulse wave wc, a magnitude of an area-gravity-center point, g, of the pulse, and a magnitude of a rising point, a, of the pulse, respectively. Hence, the determining means 88 determines arbitrary two magnitudes of the respective magnitudes of the peak b, the area-gravity-center point, and the rising point a of the carotid pulse wave wc detected by the pressure-pulse-wave sensor 54, and determines, based on the thus determined two magnitudes and the corresponding two blood-pressure values BP, constants, α and β, in the following Expression 1 representing the above relationship:

$$BP = \alpha x + \beta \quad \text{(Expression 1)}$$

(x is a magnitude of carotid pulse wave wc)

As described above, it is possible to select, when the constants α, β in Expression 1 representing the relationship are determined, arbitrary two magnitudes of the respective magnitudes of the peak b, the area-gravity-center point, and the rising point a of the carotid pulse wave wc. In the case of the arteriosclerosis evaluating apparatus 10 shown in FIG. 1, i.e., in the case where a region (e.g., the upper arm 14) where blood-pressure values BP are measured and a region (e.g., the neck portion 38) where a pulse wave is detected differ from each other, it is preferred to select the respective magnitudes of the peak b and the area-gravity-center point g and determine the constants α, β of Expression 1 based on the thus selected magnitudes of the peak b and the area-gravity-center point g and the corresponding diastolic and mean blood-pressure values $BP_{DIA}$, $BP_{MEAN}$. The reason for this is that systolic blood pressure $BP_{SYS}$ changes considerably largely among different regions of a patient whereas diastolic or mean blood pressure $BP_{DIA}$, $BP_{MEAN}$ does not change so largely.

An incident-wave-peak determining means 90 determines a magnitude of a peak, pi, of an incident-wave component, wi, which is contained in a heartbeat-synchronous pulse of the carotid pulse wave wc continuously detected by the highest-pressure detecting element EM of the pressure-pulse-wave sensor 54 in the state in which the pressing force HDP applied to the sensor 54 is maintained at the optimum pressing force HDPO. The carotid pulse wave wc contains the incident-wave component wi, indicated at broken line in FIG. 5, and the peak pi of the incident-wave component wi corresponds to an inflection point or a maximal point of the composite carotid pulse wave wc (i.e., observed wave) that occurs between a rising point, a, and a peak point, b (inclusive), of the composite wave wc. In the example shown in FIG. 5, the peak pi of the incident wave wi corresponds to an inflection point of the observed wave wc. To this end, the incident-wave-peak determining means 90 subjects the continuously obtained pressure-pulse-wave signal SM2 to a prescribed mathematical treatment, to detect an inflection point or a maximal point occurring between a rising point a and a peak point b of each heartbeat-synchronous pulse of the carotid pulse wave wc represented by the signal SM, and determines a magnitude of the inflection point or the maximal point as a magnitude of the peak pi of the incident wave wi. Here, the mathematical treatment may be a common treatment used to detect an inflection point or a maximal point; such as a differentiation treatment or a filter treatment.

Figure 5:
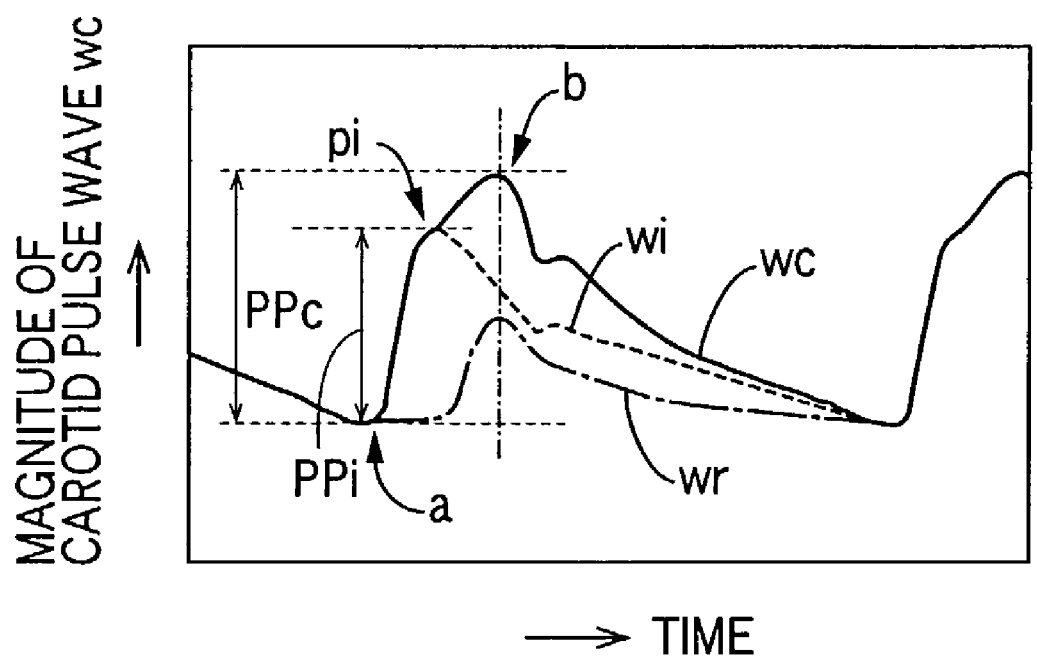
FIG. 5 is a view showing an example of a carotid pulse wave, wc, represented by a pressure-pulse-wave signal, SM2, supplied from one of the pressure-sensing elements of the pressure-pulse-wave sensor of FIG. 1.

As shown in FIG. 5, the carotid pulse wave wc additionally contains a reflected-wave component wr, indicated at one-dot chain line. It is speculated that the carotid pulse wave wc is a composite wave of (a) a pressure wave (i.e., an incident wave wi) which is produced when blood is ejected from the heart of a patient and which propagates toward a peripheral portion of the patient and (b) a reflected wave wr which is produced when the incident wave wc is reflected, and that the reflected wave wr is mainly produced around a bifurcated portion of a common iliac artery of the patient.

A reflected-wave-occurrence-time determining means 92 determines a time when a peak point of the reflected wave wr occurs, based on the carotid pulse wave wc continuously detected by the highest-pressure detecting element EM of the pressure-pulse-wave sensor 54 in the state in which the pressing force HDP applied to the sensor 54 is kept at the optimum pressing force HDPO. The time of occurrence of the peak point of the reflected wave wr is a time of occurrence of the first maximal point following the peak point pi of the incident wave wi. Therefore, in the case, shown in FIG. 5, where a peak point pi of an incident wave wi does not coincide with a peak point b of a carotid pulse wave wc, the peak point pi of the carotid pulse wave wc is determined as a peak point of a reflected wave wr. On the other hand, in the case where a peak point pi of an incident wave wi is so large that the peak point pi of the incident wave wi also defines a peak point b of a carotid pulse wave wc, a time of occurrence of the first maximal point following the peak point pi of the incident wave wi is determined as a time of occurrence of a peak point of a reflected wave wr.

A pressure-difference determining means 94 determines a pressure difference ΔP between (a) a blood pressure determined based on a magnitude of the carotid pulse wave wc at the time of occurrence of the peak point of the reflected wave wr, determined by the reflected-wave-occurrence-time determining means 92, according to the relationship represented by Expression, and (b) a blood pressure determined based on a magnitude of the peak point pi of the incident wave wi, determined by the incident-wave-peak determining means 90, according to the same relationship. However, the pressure-difference determining means 94 may be modified to first determine a magnitude difference between the magnitude of the carotid pulse wave wc at the time of occurrence of the peak point of the reflected wave wr, and the magnitude of the peak point pi of the incident wave wi, and then determine a pressure difference ΔP based on the thus determined magnitude difference according to the relationship represented by Expression 1.

Then, the pressure-difference determining means 94 operates the display device 76 to display the thus determined pressure difference ΔP, and stores, in the memory device 78, the pressure difference ΔP in association with the blood-pressure values BP determined by the blood-pressure determining means 86, in the form of a set of display information including the pressure difference ΔP and the blood-pressure values BP.

As can be understood from the fact that when an augmentation index (AI) is determined, a magnitude difference between a magnitude of a pulse wave at the time of occurrence of a peak point of a reflected wave and a magnitude of a peak point of an incident wave is used in place of a magnitude of the reflected wave, the above-indicated pressure difference ΔP can be said as the blood pressure corresponding to the magnitude of the reflected wave wr of the carotid pulse wave wc. Therefore, when the pressure difference ΔP is displayed on the display device 76, a medical person can obtain, from the pressure difference ΔP displayed, physical information different from the augmentation index that has been known as an index used to evaluate arteriosclerosis.

More specifically described, an augmentation index is a ratio of a difference between a magnitude of a peak point of an incident wave and a magnitude of an observed pulse wave at the time of occurrence of a peak point of a reflected wave, to a pulse pressure of the observed pulse wave and accordingly, even if that difference may be large because afterload acting on patient's heart is large, the augmentation index may be considerably small, if the pulse pressure is also large. Likewise, even if that difference may be small because the afterload on the heart is small, the augmentation index may be considerably large, if the pulse pressure is also small. Therefore, augmentation index cannot be used when arteriosclerosis is evaluated based on afterload acting on patient's heart. In contrast thereto, pressure difference ΔP can be said as a pressure corresponding to a reflected wave and accordingly pressure difference ΔP can be used to evaluate magnitude of afterload on patient's heart or arteriosclerosis influencing the afterload.

Figure 7:
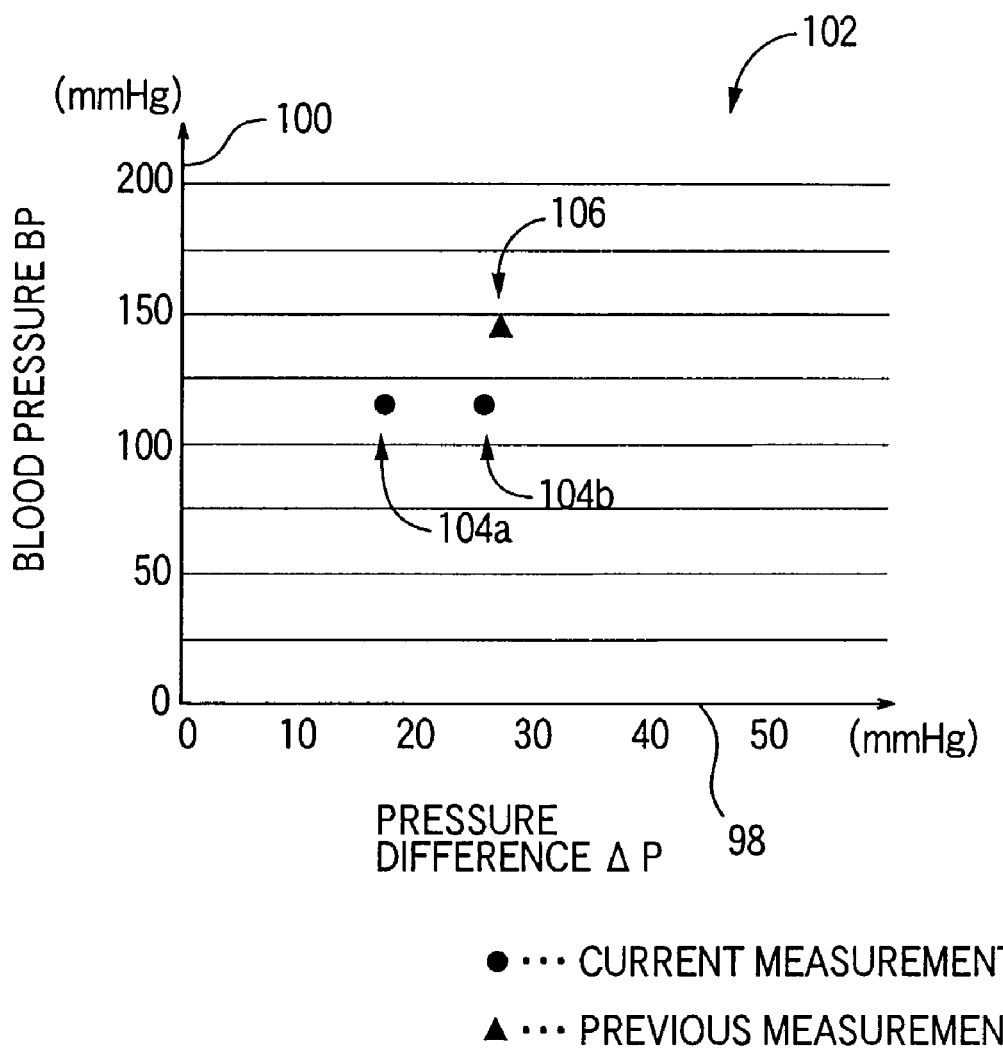
FIG. 7 is a view showing an example of a two-dimensional graph which is displayed on a display device by a graph displaying means shown in FIG. 6.

A graph displaying means 96 operates the display device 76 to display a two-dimensional graph 102 having a pressure-difference axis 98 and a blood-pressure axis 100, as shown in FIG. 7. In addition, the graph displaying means 96 operates the display device 76 to display, in the two-dimensional graph 102, a symbol 104 at a position (i.e., coordinates) corresponding to the set of display information, stored in the memory device 78, that includes the blood-pressure value BP measured in the current measuring operation, and the pressure difference ΔP determined in the current operation. Any of the systolic, mean, and diastolic blood-pressure values $BP_{SYS}$, $BP_{MEAN}$, $BP_{DIA}$ may be selected, and a prescribed one of the three blood-pressure values BP is used to display the symbol 104 on the display device 76. FIG. 7 shows two symbols 104a, 104b each corresponding to the current measuring operation, just for the purpose of explaining two cases, below. In fact, the display device 76 displays only a single symbol 104 corresponding to each measuring operation.

If the memory device 78 stores one or more previous sets of display information that had been obtained in one or more previous measuring operations from the patient identified by the patient identifying means 79, the graph displaying means 96 operates the display device 76 to display one or more symbols at one or more positions corresponding to the one or more previous sets of display information, such that each of the symbols corresponding to the previous measurements is distinguishable from each other and from the symbol 104 corresponding to the current measurement. FIG. 7 shows an example in which the display device 76 displays the symbol 104 corresponding to the pressure difference ΔP and the blood-pressure value BP obtained in the current measurement, and a symbol 106 corresponding to the pressure difference ΔP and the blood-pressure value BP obtained in the previous measurement.

When the display device 76 displays, in the two-dimensional graph 102, the symbol 104 corresponding to the current measurement and the symbol 106 corresponding to the previous measurement, a medical person such as a doctor can observe a degree of efficacy of a treatment against arteriosclerosis of the patient. In many cases, as arteriosclerosis advances, hypertension also occurs and even myocardial infarction may occur. To treat those diseases, antihypertensive drug (vasodilator) may be used to dilate blood vessels and thereby lower blood pressure. When the virtue of this vasodilator presents, the blood vessels dilate and the resistance thereof lowers, and accordingly the blood pressure lowers. Thus, pressure difference ΔP and blood pressure BP should also lower. If both pressure difference ΔP and blood pressure values BP lower as indicated at the symbol 104a in FIG. 7, it can be judged that the virtue of the vasodilator is present. Meanwhile, there is known a central antihypertensive drug that lowers blood pressure of a central side (the heart) of a patient, and this drug may be used with the above-indicated vasodilator. When the central antihypertensive drug is used to lower the blood pressure, the resistance of blood vessels does not change so largely, and accordingly the amount of change of pressure difference ΔP with respect to the amount of change of blood pressure BP is small. Therefore, if the amount of change of pressure difference ΔP with respect to the amount of change of blood pressure BP is small as indicated at the symbol 104b, it can be judged that the blood pressure is lowered by the central antihypertensive drug.

Figure 8:
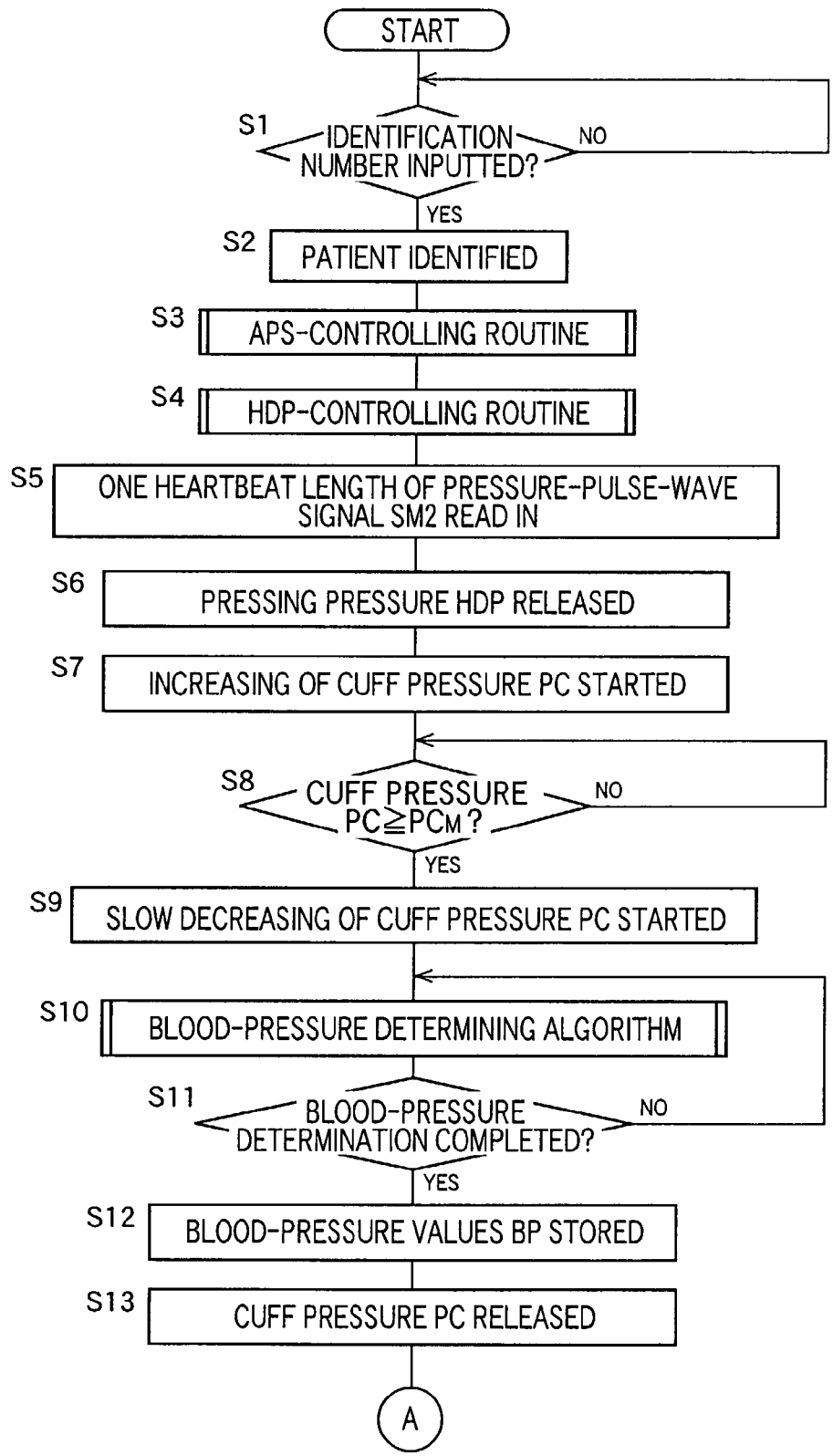
FIG. 8 is a flow chart for explaining more concretely a portion of the control functions of a CPU (central processing unit) of the control device, shown in FIG. 6.
Figure 9:
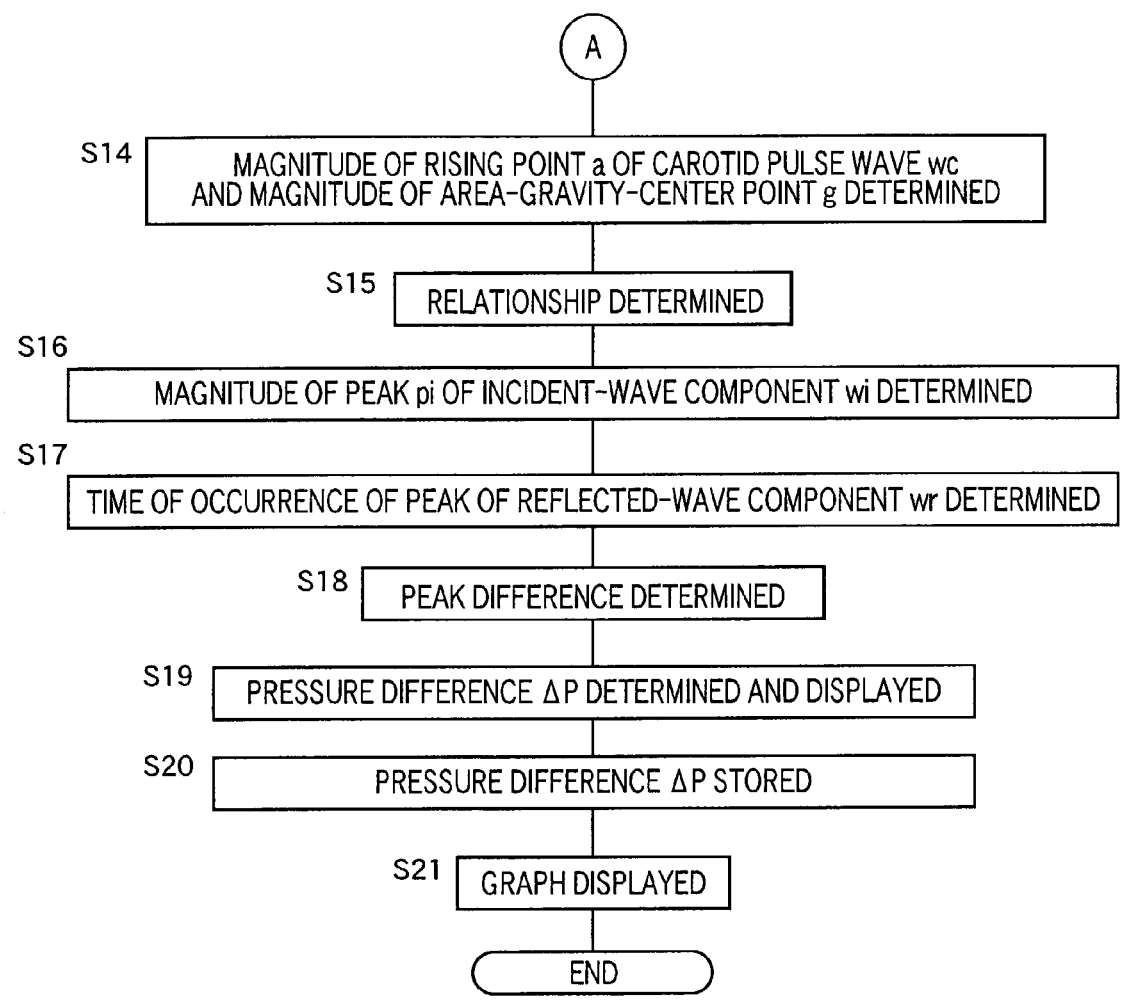
FIG. 9 is a flow chart for explaining more concretely another portion of the control functions of the CPU, shown in FIG. 6.

FIGS. 8 and 9 are flow charts representing the control functions of the CPU 70, shown in the diagrammatic view of FIG. 6.

In FIG. 8, first, the CPU carries out Steps S1 and S2 (hereinafter, the term "Step(s)" is omitted, if appropriate) corresponding to the patient identifying means 79. At S1, the CPU judges whether the CPU has received an identification number of a patient from the input device 77. If a positive judgment is made at S1, the control goes to S2 to identify, based on the identification number inputted through the input device, the patient from which blood-pressure values BP and pressure difference ΔP are to be measured.

Then, the control goes to S3 corresponding to the optimum-pressing-position determining means 80, i.e., an APS-controlling routine. In this routine, the CPU operates the widthwise-direction moving device 64 to move the pressure-pulse-wave sensor 54 to an optimum pressing position where one of the pressure-sensing elements E that detects the highest pressure is located at substantially the middle of the array of elements E, and determines the one pressure-sensing element E as a highest-pressure sensing element EM.

Subsequently, the control goes to S4 corresponding to the pressing-force determining means 82, i.e., an HDP-controlling routine. More specifically described, the CPU operates the pressure control valve 60 so that the pressing force HDP applied to the pressure-pulse-wave sensor 54 is continuously increased. During this increasing of the pressing force HDP, the CPU determines an optimum pressing force HDPO at which the pressure pulse wave detected by the above-described highest-pressure detecting element EM shows the greatest amplitude, and maintains the pressing force HDP applied to the pressure-pulse-wave sensor 54, at the thus determined optimum pressing force HDPO. Then, the control goes to S5 where the CPU reads in one heartbeat-synchronous pulse of the pressure-pulse-wave signal SM2. Then, the control goes to S6 to stop the air pump 58 and operate the pressure control valve 60 so that the pressing force HDP applied to the pressure-pulse-wave sensor 54 is decreased to an atmospheric pressure.

Then, at S7, the CPU starts the air pump 24 and operate the pressure control valve 18 so as to start quickly increasing the cuff pressure PC. Subsequently, at S8, the CPU judges whether the cuff pressure PC has exceeded a target pressure $PC_M$ pre-set at 180 mmHg. S8 is repeated until a positive judgment is made, while the cuff pressure PC is quickly increased. Meanwhile, if a positive judgment is made at S8, the control goes to S9 to stop the air pump 24 and operate the pressure control valve 18 so as to start slowly decreasing the cuff pressure PC at a rate of about 3 mmHg/sec.

Next, the control goes to S10 to S12 corresponding to the blood-pressure determining means 86. At S10, the CPU determines, based on change of respective amplitudes of successive heartbeat-synchronous pulses of the upper-arm pulse wave represented by the cuff-pulse-wave signal SM1 continuously obtained during the slow decreasing of the cuff pressure PC, a systolic blood pressure $BP_{SYS}$, a mean blood pressure $BP_{MEAN}$, and a diastolic blood pressure $BP_{DIA}$ of the patient, according to well-known oscillometric blood-pressure determining algorithm. Then, at S10, the CPU judges whether the determination of the blood-pressure values BP has completed at S10. Since the diastolic blood pressure $BP_{DIA}$ is last determined at S10, the CPU judges, at S11, whether the diastolic blood pressure $BP_{DIA}$ has been determined. S10 is repeated until a positive judgment is made at S11, while the blood-pressure determining algorithm is continued. Meanwhile, if a positive judgment is made at S11, the control goes to S12 to store, in the memory device 78, the systolic, mean, and diastolic blood-pressure values $BP_{SYS}$, $BP_{MEAN}$, $BP_{DIA}$ determined at S10 and S11, as the blood-pressure values BP of the patient identified at S2, together with data indicative of a date and a time when the blood-pressure values BP are measured.

Then, at S13, the CPU operates the pressure control valve 18 to decrease the cuff pressure PC to an atmospheric pressure. In the present flow chart, S7 to S9 and S13 correspond to the cuff-pressure changing means 84.

Next, S14 and the following steps shown in FIG. 9 will be described. S14 and S15 correspond to the relationship determining means 88. At S14, the CPU determines respective magnitudes of a rising point, a, and an area-gravity-center point, g, of the one heartbeat-synchronous pulse of the carotid pulse wave wc, read in at S5. Then, at S15, the CPU determines the two constants, α and β, of the above-indicated Expression 1, based on an equation obtained by substituting the magnitude of the rising point a determined at S14 and the diastolic blood pressure $BP_{DIA}$ determined at S10, for Expression 1, and an equation obtained by substituting the magnitude of the area-gravity-center point g determined at S14 and the mean blood pressure $BP_{MEAN}$ determined at S10, for Expression 1.

Next, the control goes to S16 corresponding to the incident-wave-peak determining means 90. At S16, the CPU subjects, to a fourth-order differentiation treatment or analysis, a portion or length of the pressure-pulse-wave signal SM1, read in at S5, that continues from a time corresponding to the rising point a of the carotid pulse wave wc and to a time corresponding to the peak b of the same wave, and thereby determines an inflection point or a maximal point occurring to the length of the signal SM1, and determines a magnitude of the thus determined inflection or maximal point as a magnitude of a peak pi of an incident wave wi.

Then, the control goes to S17 corresponding to the reflected-wave-occurrence-time determining means 92, where the CPU determines a time of occurrence of a peak point of a reflected wave wr of the one pulse of the carotid pulse wave wc represented by the pressure-pulse-wave signal SM1 read in at S5. More specifically described, if the magnitude of the peak point pi of the incident wave wi determined at S16 does not coincide with the greatest magnitude of the observed carotid pulse wave wc, a time of occurrence of the greatest magnitude (i.e., the peak b) of the carotid pulse wave wc is determined as the time of occurrence of the peak point of the reflected wave wr; and if the magnitude of the peak point pi of the incident wave wi coincides with the greatest magnitude of the observed carotid pulse wave wc, a time of occurrence of the first maximal magnitude following the peak point pi of the incident wave wi is determined as the time of occurrence of the peak point of the reflected wave wr.

Subsequently, the control goes to S18 to S20 corresponding to the pressure-difference determining means 94. First, at S18, the CPU calculates a difference value by subtracting the magnitude of the peak point pi of the incident wave wi, determined at S16, from the magnitude of the carotid pulse wave wc at the time of occurrence of the peak point of the reflected wave wr, determined at S16. Then, at S19, the CPU determines a pressure difference ΔP by substituting the difference value determined at S18, for the relationship represented by Expression 1 determined at S15, and operates the display device 76 to display the thus determined pressure difference ΔP. Then, at S20, the CPU stores, in the memory device 78, a set of display information including the pressure difference ΔP determined at S19 and the blood-pressure values BP stored at S12.

Then, the control goes to S21 corresponding to the graph displaying means 96. At S21, the CPU operates the display device 76 to display the two-dimensional graph 102 shown in FIG. 7 and display, in the graph 102, a symbol 114 at a position defined by the pressure difference ΔP and the blood pressure BP respectively stored in the memory device 78 at S20 and S12, and a symbol 116 at a position defined by the past pressure difference ΔP and blood pressure BP stored in the memory device 78 for the patient identified at S2.

In the embodiment employing the above-described flow charts, the control device 32 determines, at S18 and S19 (the pressure-difference determining means 94), the pressure difference ΔP between (a) the blood pressure BP determined based on the magnitude of the carotid pulse wave wc at the time of occurrence of the peak point of the reflected wave wr, determined at S17 (the reflected-wave-occurrence-time determining means 92), and (b) the blood pressure BP determined based on the magnitude of the peak point pi of the incident wave wi of the carotid pulse wave wc. This pressure difference ΔP can be used as the pressure corresponding to the reflected wave wr. Therefore, a person can evaluate afterload acting on patient's heart, based on the pressure difference ΔP displayed on the display device 76. In addition, since large afterload indicates advanced arteriosclerosis, the person can evaluate arteriosclerosis of the patient based on the pressure difference ΔP.

Moreover, in the embodiment employing the above-described flow charts, the control device 32 stores, in the memory device 78, the set of display information including the pressure difference ΔP determined at S18 and S19 (the pressure-difference determining means 94), and the blood pressure BP measured by the blood-pressure measuring device 35; and operates, at S21 (the graph displaying means 96), the display device 76 to display, in the two-dimensional graph 102, the symbols 104, 104 at the respective positions defined by the sets of display information stored in the memory device 78. Thus, in each of the second and following measuring operations, a person can easily recognize the time-wise change of pressure difference ΔP with respect to the time-wise change of blood pressure BP. Therefore, the person can easily evaluate effectiveness of medical treatment against arteriosclerosis.

While the present invention has been described in its preferred embodiment by reference to the drawings, it is to be understood that the invention may otherwise be embodied.

For example, in the illustrated arteriosclerosis evaluating apparatus 10, the blood-pressure values BP are obtained as the blood-pressure-related information, and the axis of ordinate of the two-dimensional graph 102 is the blood-pressure axis 100. However, since it is known that pulse-wave-propagation-velocity-related information that is related to a velocity at which a pulse wave propagates between two portions of a living subject; such as pulse-wave propagation velocity or pulse-wave propagation time, changes in relation with blood pressure, pulse-wave-propagation-velocity-related information may be obtained as the blood-pressure-related information. In this case, the axis of ordinate of the two-dimensional graph 102 may be an axis indicative of pulse-wave-propagation-velocity-related information. Moreover, since it is known that the above-described augmentation index is correlated to the pulse-wave propagation velocity, augmentation index may be used as the blood-pressure-related information.

In the illustrated embodiment, the blood-pressure values BP determined by the blood-pressure determining means 86 and the pressure difference ΔP determined by the pressure-difference determining means 94 are once stored in the memory device 78, and the graph displaying means 96 displays the symbol 104 based on the blood-pressure values BP and the pressure difference ΔP stored in the memory device 78. However, since the RAM 74 is a memory device that has a temporary-memory function, the blood-pressure values BP and the pressure difference ΔP may be stored in the RAM 74, and the graph displaying means 96 displays the symbol 104 based on the blood-pressure values BP and the pressure difference ΔP stored in the RAM 74.

In the illustrated arteriosclerosis evaluating apparatus 10, the pressure-pulse-wave detecting probe 36 as the pressure-pulse-wave detecting device is employed as the pulse-wave detecting device. However, a volumetric-pulse-wave detecting device such as a photoelectric-pulse-wave detecting probe for use in oxygen-saturation measurement may be employed as the pulse-wave detecting device.

In addition, the illustrated arteriosclerosis evaluating apparatus 10, the pressure-pulse-wave detecting probe 36 is employed as the pulse-wave detecting device. However, since the cuff-pulse-wave signal SM1 extracted by the pulse-wave filter circuit 35 represents an upper-arm pulse wave, the blood-pressure measuring device 35 may be used as the the pressure-pulse-wave detecting probe 36 as the pressure-pulse-wave detecting device is employed as the pulse-wave detecting device.

The present invention may be embodied with other various changes without departing from the spirit of the invention.

What is claimed is:

1. An apparatus for evaluating arteriosclerosis of a living subject, comprising:
   a blood-pressure measuring device which measures at least one blood-pressure value of the subject;
   a pulse-wave detecting device which detects a pulse wave from a portion of the subject;
   a relationship determining means for determining a relationship between pulse-wave magnitude and blood pressure, based on at least one magnitude of the pulse wave detected by the pulse-wave detecting device and said at least one blood-pressure value measured by the blood-pressure measuring device;
   an incident-wave-peak determining means for determining a magnitude of a peak point of an incident-wave component which is contained in the pulse wave detected by the pulse-wave detecting device;
   a reflected-wave-occurrence-time determining means for determining a time of occurrence of a peak point of a reflected-wave component which is contained in the pulse wave detected by the pulse-wave detecting device;
   a pressure-difference determining means for determining, according to the relationship between pulse-wave magnitude and blood pressure determined by the relationship determining means, a pressure difference corresponding to a magnitude difference between a magnitude of the pulse wave at the time of occurrence of the peak point of the reflected-wave component determined by the reflected-wave-occurrence-time determining means, and the magnitude of the peak point of the incident-wave component determined by the incident-wave-peak determining means; and
   a display device which displays the pressure difference determined by the pressure-difference determining means.

2. An apparatus according to claim 1, further comprising:
   a blood-pressure-related-information obtaining device which obtains blood-pressure-related information which changes in relation with blood pressure of the subject;
   a memory device which stores a plurality of sets of display information each of which includes a pressure difference determined by the pressure-difference determining means and a piece of blood-pressure-related information obtained by the blood-pressure-related-information obtaining device and; and
   a graph displaying means for operating the display device to display a two-dimensional graph defined by a first axis indicative of pressure difference and a second axis indicative of blood-pressure-related information, and additionally display, in the two-dimensional graph, a plurality of symbols at a plurality of positions, respectively, which correspond to said plurality of sets of display information, respectively, that are stored by the memory device.

3. An apparatus according to claim 2, further comprising an input device which is operable by an operator to input identification information identifying the subject.

4. An apparatus according to claim 3, further comprising a subject identifying means for identifying the subject based on the identification information inputted through the input device, wherein the memory device stores the plurality of sets of display information for the subject identified by the subject identifying means.

5. An apparatus according to claim 1, wherein the pulse-wave detecting device comprises a pressure-pulse-wave sensor which is adapted to be pressed against an artery of the portion of the subject and detects, as the pulse wave, a pressure pulse wave produced from the artery.

6. An apparatus according to claim 1, wherein the incident-wave-peak determining means determines the peak point of the incident-wave component, by differentiating the pulse wave detected by the pulse-wave detecting device.

7. An apparatus according to claim 6, wherein the incident-wave-peak determining means comprises:
   means for determining a rising point and a peak point of a heartbeat-synchronous pulse of the pulse wave detected by the pulse-wave detecting device;
   means for differentiating a portion of the pulse wave between the rising point and the peak point; and
   means for determining, as the peak point of the incident-wave component, an inflection point or a maximal point of the differentiated portion of the pulse wave.

8. An apparatus according to claim 1, wherein the reflected-wave-occurrence-time determining means comprises:
   means for differentiating the pulse wave detected by the pulse-wave detecting device; and
   means for determining, as the peak point of the reflected-wave component, an earliest maximal point of the pulse wave that appears after the peak point of the incident-wave component.

9. An apparatus according to claim 1, wherein the blood-pressure measuring device measures a diastolic blood-pressure value and a mean blood-pressure value of the subject, and the relationship determining means determines respective magnitudes of a rising point and an area-gravity-center point of a heartbeat-synchronous pulse of the pulse wave detected by the pulse-wave detecting device, and determines, as the relationship between pulse-wave magnitude and blood pressure, a linear function based on the respective magnitudes of the rising point and the area-gravity-center point of the pulse wave and the diastolic and mean blood-pressure values.

* * * * *